United States Patent [19]

Nemet-Mavrodin

[11] Patent Number: 4,861,933
[45] Date of Patent: * Aug. 29, 1989

[54] PROCESS FOR CONVERTING ALIPHATICS TO AROMATICS OVER A GALLIUM-ACTIVATED ZEOLITE

[75] Inventor: Margaret Nemet-Mavrodin, Cherry Hill, N.J.

[73] Assignee: Mobil Oil Corp., New York, N.Y.

[ * ] Notice: The portion of the term of this patent subsequent to Feb. 28, 2006 has been disclaimed.

[21] Appl. No.: 240,299

[22] Filed: Sep. 6, 1988

Related U.S. Application Data

[63] Continuation-in-part of Ser. No. 89,194, Aug. 25, 1987, abandoned, which is a continuation-in-part of Ser. No. 133,773, Dec. 16, 1987, Pat. No. 4,808,295.

[51] Int. Cl.$^4$ ............................................. C07C 2/52
[52] U.S. Cl. ..................................... 585/417; 585/419
[58] Field of Search ................... 208/65; 585/417, 419, 585/412

[56] References Cited

U.S. PATENT DOCUMENTS

| | | |
|---|---|---|
| 4,180,689 | 12/1979 | Davis et al. .......................... 585/415 |
| 4,304,686 | 12/1981 | Telford ................................. 502/61 |
| 4,334,114 | 6/1982 | Ellis ..................................... 585/407 |
| 4,350,835 | 9/1982 | Chester et al. ....................... 585/415 |
| 4,487,843 | 12/1984 | Telford et al. ........................ 502/85 |

FOREIGN PATENT DOCUMENTS

| | | |
|---|---|---|
| 0050021 | 4/1982 | European Pat. Off. . |
| 0147111 | 7/1985 | European Pat. Off. . |
| 0216491 | 4/1987 | European Pat. Off. . |

*Primary Examiner*—Curtis R. Davis
*Attorney, Agent, or Firm*—Alexander J. McKillop; Charles J. Speciale; Dennis P. Santini

[57] ABSTRACT

A catalytic process is provided for converting a $C_3+$ feedstock containing at least 50 wt. % of $C_3$ to $C_{12}$ aliphatic hydrocarbons to aromatics by contacting the feedstock under conversion conditions of a severity resulting in a conversion of at least about 80 wt. % of said hydrocarbons, with a catalyst prepared by loading with gallium a zeolite having a Constraint Index within the approximate range of 1 to 12 and a silica/alumina molar ratio of about 25:1 to 1000:1, and subsequently calcining the catalyst at a temperature of at least about 700° C.

14 Claims, No Drawings

PROCESS FOR CONVERTING ALIPHATICS TO AROMATICS OVER A GALLIUM-ACTIVATED ZEOLITE

CROSS REFERENCE TO RELATED APPLICATIONS

This application is a continuation-in-part of application Ser. Nos. 89,194, filed Aug. 25, 1987, and now abandoned, and 133,773, filed Dec. 16, 1987, and now U.S. Pat. No 4,808,295.

BACKGROUND OF THE INVENTION

1. Field of the Invention

This invention relates to a process for the conversion of a $C_3^+$ feedstock containing a major proportion of $C_3$ to $C_{12}$ aliphatic hydrocarbons to aromatics in the presence of a zeolite catalyst containing gallium.

2. Background Information

Zeolites and alumina have been used in the past in preparation of catalysts for the production of aromatic hydrocarbons from aliphatic hydrocarbons by passing the aliphatic hydrocarbon over the catalyst at an elevated temperature in the liquid or vapor phase. Zeolites of various types have been suggested for the preparation of such catalysts, containing gallium which has been impregnated on the zeolite substrate, or as ions for which the original cations have been exchanged. However, it has sometimes been considered desirable to improve the yields of aromatic hydrocarbons when using such catalysts.

U.S. Pat. Nos. 4,180,689 and 4,334,114 teach processes for the production of aromatics by contacting a $C_3$–$C_{12}$ hydrocarbon feedstock with a catalyst in which gallium is supported on an aluminosilicate, e.g. ZSM-5. After addition of the gallium, the catalyst is activated at a temperature of between 400° and 650° C.

U.S. Pat. No. 4,304,686 teaches the aromatization of aliphatic hydrocarbons utilizing as catalyst a zeolite having a silica/alumina molar ratio of 10:1 to 500:1 in which at least some of the cations have been exchanged for gallium ions. The zeolite is calcined at a temperature of at least 300° C., suitably between 300° and 800° C., before being treated to effect the gallium exchange.

U.S. Pat. No. 4,350,835 teaches a catalytic process for converting a feedstock comprising a high percentage of ethane to aromatics employing as a catalyst a zeolite, e.g., ZSM-5, with a silica/alumina ratio of at least 12 and having incorporated therein a minor amount of gallium. The zeolite is calcined at 540° C. before the incorporation of the gallium.

European Patent Specification Publication No. 50,021 teaches a process for producing aromatic hydrocarbons by contacting a feedstock containing at least 70% weight of $C_2$ hydrocarbons with a catalyst comprising an aluminosilicate, e.g., ZSM-5, with a silica/alumina molar ratio of at least 5:1, and in which either gallium is deposited thereon, or cations have been exchanged with gallium ions. After incorporation of the gallium, the catalyst is activated at a temperature of between 400° C. and 650° C.

U.S. Pat. No. 4,487,853 discloses the conversion of hydrocarbon feedstocks to aromatics using a catalyst subjected during its preparation to a steam treatment followed by loading with a Group IIIb metal, especially gallium. The catalyst may also be calcined under dry conditions at or about 550° C. one or more times in the course of its preparation. However, the publication states that "if the calcination stage during the preparation of a zeolite is carried out at or about 550° C. under substantially dry conditions, the resulting catalysts have a high initial activity in hydrocarbon conversion reactions but also produce coke at a high rate and therefore deactivate rapidly."

European Patent application Publication No. 147,111, published July 3, 1985, discloses the production of aromatic hydrocarbons from a feedstock comprising $C_3/C_4$ hydrocarbons mixed with $C_2$ hydrocarbons, especially ethane, by contacting the feedstocks at a temperature below 580° C. with a gallium-load zeolite, e.g., ZSM-5. The catalyst may be subjected to a controlled deactivation by a dry calcination at a temperature above 600° C., preferably 700°–900° C.

European Patent application Publication No. 216,491, published Apr. 1, 1987, discloses the production of aromatic hydrocarbons from a feedstock containing a major proportion of methane by contacting it with a catalyst which may be a gallium-loaded zeolite such as ZSM-5. Prior to contact with the hydrocarbon feedstock, the catalyst whether or not loaded with gallium, may be heat treated at a temperature of from 400° C. to 850° C.

Pending application Ser. No. 882,875, filed July 7, 1986 by C. T-W. Chu, and now abandoned, teaches the conversion of $C_3$ to $C_{12}$ aliphatic hydrocarbons to aromatics using as catalyst a zeolite, e.g., ZSM-5, having a silica/alumina molar ratio of at least 550. The catalyst is activated by calcining in air at about 540° C.

Pending application Ser. No. 882,863, filed July 7, 1986 by C. T-W. Chu, and now abandoned, covers the conversion of $C_2$ to $C_{12}$ aliphatic hydrocarbons to aromatics using as catalyst a zeolite, e.g., ZSM-5, containing zeolitic gallium in tetrahedral coordination therein. The catalyst may be activated by base exchange with ammonium ions followed by calcination at 538° C.

SUMMARY OF THE INVENTION

Briefly stated, this invention comprises a process for producing desirable aromatic compounds including contacting a $C_3^+$ feedstock containing a major proportion, i.e., at least 50 wt. %, of $C_3$–$C_{12}$ aliphatic hydrocarbons, with a gallium loaded type crystalline aluminosilicate zeolite catalyst, which has been calcined at a temperature of at least 700° C. after the incorporation of the gallium, under conversion conditions of a severity resulting in a conversion of at least about 80 wt. % of said aliphatic hydrocarbons. It has been found that use of the described catalyst results in a higher selectivity to BTX aromatics than a similar catalyst which was not exposed to such high temperatures after loading with gallium. Furthermore, a similar catalyst which is calcined at a similar temperature prior to loading with gallium is significantly less active than the catalyst used in the process of this invention.

DESCRIPTION OF SPECIFIC EMBODIMENTS

The zeolite on which gallium is loaded in producing the catalyst used in the process of this invention, may be prepared by any of the methods known in the art. Thus, variations of the original method for the production of this type of zeolite utilizing an "organic template" provided by the presence of organic cations, are disclosed in U.S. Pat. Nos. 3,702,886 and Re. No. 29,948, and European Patent Application No. 130,809. Alternatively, the zeolite may be prepared without employing any organic cations, but utilizing instead seeds of the desired zeolite in the formulating mixture which seeds themselves were formed in the presence of organic ions or from other seeds formed in the presence of organic ions, etc., as disclosed, for example, in U.S. Pat. Nos. 4,175,114; 4,199,556; and 4,341,748. Moreover, the zeolites contemplated in the process of this invention may be formed in the absence of any organic ions or seeds of the type described, utilizing instead as precursor a silica or aluminosilicate which is precipitated or crystallized from solution or homogeneous amorphous phase and having certain characteristics, as disclosed, for example in pending application Ser. No. 14,147, filed Feb. 12, 1987, and now abandoned, or European Patent Application No. 106,552 the entire disclosures of which are incorporated by reference. Other methods for the preparation of the desired zeolites, i.e. zeolites having X-ray diffraction patterns typical of such zeolites, are disclosed in the art and may also be used. In general, the zeolite should be prepared using any of the foregoing methods so that the silica/alumina molar ratio of the zeolite is in the range of about 25:1 to about 1000:1.

The process of the present invention may be carried out using catalysts in which gallium is impregnated on the surface of the zeolite or is ion-exchanged with the cations of the zeolite using techniques of impregnation or ion-exchange which are well-known in the art. For example, the gallium may be impregnated on the surface of the zeolite by preparing a solution, e.g., an aqueous solution of a gallium compound such as gallium nitrate and adding to this solution a preshaped form of the desired zeolite such as 1/16 in. extrudates with alimina as a binder, or in the form of a fluid bed powder, and allowing the zeolite to be thoroughly contacted with the gallium solution. The contacted catalyst is then dried under vacuum at a moderate temperature (90°-100° C.). After calcination, the zeolite contains gallium impregnated on its surface in the form of gallium oxide.

The gallium in the catalyst composition is present as ions if the cations in the alumimosilicate support have been exchanged with gallium ions. In this case, the gallium ions are suitably provided as an aqueous solution of a gallium salt such as for instance gallium sulfate, nitrate, or chloride. Such catalysts may be produced by conventional ion exchange techniques and the catalysts so produced are subsequently dried. For example, an aqueous solution of gallium compound such as gallium sulfate may be placed in contact with the ammonium form of a preshaped form of the zeolite at ambient or elevated temperature, e.g., by refluxing. The exchanged zeolite is then separated by recantation followed by filtration, washed several times with deionized water and finally dried.

When the catalyst composition is prepared by using a compound of gallium-comprising metal which ionizes in aqueous solution, for example gallium nitrate, some of the gallium ions are generally exchanged with the cations in the zeolite even if the preparation was directed to impregnation.

Whichever method of catalyst preparation is used, the amount of gallium present in the total catalyst composition, may vary, for example between about 0.5 and 5 percent by weight, preferably between about 0.5 and 2.0 percent by weight. Elements other than gallium may also be present, such as any of various suitable metals in Groups I through VIII of the Periodic Table including by way of example zinc, platinum, rhenium, cobalt, titanium, tellurium, sodium, nickel, chromium, aluminum, copper, platinum, calcium and rare earth metals or other modifiers, such as phosphorus. In general, the amount of gallium added to the zeolite will be more than 50% by weight of the total added metal.

As stated, for purposes of this invention the gallium-loaded zeolite catalyst must be calcined at a temperature of at least about 700° C., before being used as a catalyst for the aromatization of aliphatic compounds. Preferably the catalyst is calcined at a temperature of at least about 775° C., and more preferably at least about 800° C. For example, the catalyst may be heated at a temperature of about 800° to 825° C. for a period of about 1 to 1.5 hours prior to use.

The silica/alumina ratio referred to may be determined by conventional analysis. This ratio is meant to represent, as closely as possible, the ratio in the rigid anionic framework of the zeolite crystal and to exclude aluminum in the binder or in cationic or other form within the channels. Zeolites having a silica/alumina molar ratio near the high point of the contemplated range, e.g., approaching 1000, may be prepared as-synthesized, or by decreasing the aluminum content of low silica to alumina ratio zeolites by steaming, dealuminizing or framework exchange procedures.

The members of the class of zeolites useful herein have an effective pore size of generally about 5 to about 8 angstroms, such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolites is not of the desired type. Windows of 10-membered rings are preferred, although, in some instances, excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons, and therefore, it is not the present intention to entirely judge the usefulness of the particular zeolite solely from theoretical structural considerations.

A convenient measure of the extent to which a zeolite provides control to molecules of varying sizes to its internal structure is the Constraint Index of the zeolite. Zeolites which provide a highly restricted access to and egress from its internal structure have a high value for the Constraint Index, and zeolites which provide relatively free access to the internal zeolite structure have a low value for the Constraint Index, and usually pores of large size, e.g. greater than 8 angstroms. The method by which Constraint Index is determined is described fully in U.S. Pat. No. 4,016,218, incorporated herein by reference for details of the method.

Constraint Index (CI) values for some typical materials are:

|        | CI (at test temperature) |
|--------|--------------------------|
| ZSM-4  | 0.5 (316° C.)            |
| ZSM-5  | 6–8.3 (371° C.–316° C.)  |
| ZSM-11 | 5–8.7 (371° C.–316° C.)  |

-continued

| | CI (at test temperature) |
|---|---|
| ZSM-12 | 2 3 (316° C.) |
| ZSM-20 | 0.5 (371° C.) |
| ZSM-22 | 7.3 (427° C.) |
| ZSM-23 | 9.1 (477° C.) |
| ZSM-34 | 50 (371° C.) |
| ZSM-35 | 4.5 (454° C.) |
| ZSM-38 | 2 (510° C.) |
| ZSM-48 | 3.5 (538° C.) |
| ZSM-50 | 2.1 (427° C.) |
| TMA Offretite | 3.7 (316° C.) |
| TEA Mordenite | 0.4 (316° C.) |
| Clinoptilolite | 3.4 (510° C.) |
| Mordenite | 0.5 (316° C.) |
| REY | 0.4 (316° C.) |
| Amorphous Silica-alumina | 0.6 (538° C.) |
| Dealuminized Y | 0.5 (510° C.) |
| Erionite | 38 (316° C.) |
| Zeolite Beta | 0.6–2.0 (316° C.–399° C.) |

The above-described Constraint Index is an important and even critical definition of these zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operations (conversion) and the presence or absence of binders. Likewise, other variables, such as crystal size of the zeolite, the presence of occluded contaminants, etc., may affect the Constraint Index. Therefore, it will be appreciated that it may be possible to so select test conditions, e.g., temperature, as to establish more than one value for the Constraint Index of a particular zeolite. This explains the range of Constraint Indices for some zeolites, such as ZSM-5, ZSM-11 and Beta.

It is to be realized that the above CI values typically characterize the specified zeolites, but that such are the cumulative result of several variables useful in the determination and calculation thereof. Thus, for a given zeolite exhibiting a CI value within the range of 1 to 12, depending on the temperature employed during the test method within the range of 290° C. to about 538° C., with accompanying conversion between 10% and 60%, the CI may vary within the indicated range of 1 to 12. Likewise, other variables such as the crystal size of the zeolite, the presence of possibly occluded contaminants and binders intimately combined with the zeolite may affect the CI. It will accordingly be understood to those skilled in the art that the CI, as utilized herein, while affording a highly useful means for characterizing the zeolites of interest is approximate, taking into consideration the manner of its determination, with the possibility, in some instances, of compounding variable extremes. However, in all instances, at a temperature within the above-specified range of 290° C. to about 538° C., the CI will have a value for any given zeolite of interest herein within the approximate range of 1 to 12.

The class of zeolites defined herein is exemplified by ZSM-5, ZSM-11, ZSM-12, ZSM-23, ZSM-35, ZSM-38, ZSM-48, and other similar materials. The compositions, methods of preparation, and X-ray diffraction patterns of these zeolites are typified in the following patents: ZSM-5 in the U.S. Pat. Nos. 3,702,886 and Re. 29,948; ZSM-11 in U.S. Pat. No. 3,709,979; ZSM-12 in U.S. Pat. No. 3,832,449; ZSM-23 in U.S. Pat. No. 4,076,842; ZSM-35 in U.S. Pat. No. 4,016,245; ZSM-38 in U.S. Pat. No. 4,046,859 and ZSM-48 in U.S. Pat. No. 4,350,835.

The entire disclosures of these patents are incorporated by reference insofar as their disclosures are necessary to identify the respective zeolites.

It is to be understood that by incorporating by reference the foregoing patents to describe examples of specific members of the novel class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is at least 25 and may be as high as about 1000. The incorporation of the identified patents should therefore not be construed as limiting the disclosed crystalline zeolites to those having the specific silica/alumina mole ratios discussed therein, it now being known that such zeolites may have higher silica/alumina ratios and yet, having the same crystal structure as the disclosed materials, may be useful or even preferred in some applications. It is the crystal structure, as identified by the X-ray diffraction "fingerprint", which establishes the identity of the specific crystalline zeolite material.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35, ZSM-38 and ZSM-48, with ZSM-5 being particularly preferred.

In a preferred aspect of this invention, the zeolites hereof are selected as those providing among other things a crystal framework density, in the dry hydrogen form, of not less than about 1.6 grams per cubic centimeter. Therefore, the preferred zeolites useful with respect to this invention are those having a Constraint Index as defined above of about 1 to about 12, a silica to alumina mole ratio of at least about 25 and up to about 1000 and a dried crystal density of not less than about 1.6 grams per cubic centimeter. The dry density for known structures may be calculated from the number of silicon plus aluminum atoms per 1000 cubic angstroms, as given, e.g., on Page 19 of the article ZEOLITE STRUCTURE by W. M. Meier. This paper, the entire contents of which are incorporated herein by reference, is included in PROCEEDINGS OF THE CONFERENCE ON MOLECULAR SIEVES, (London, April 1967) published by the Society of Chemical Industry, London, 1968.

When the crystal structure is unknown, the crystal framework density may be determined by classical pycnometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

|  | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

In utilizing the catalyst of this invention, it may be advantageous to incorporate the zeolite, prior to modification with gallium, with a matrix comprising another material resistant to the temperature and other conditions employed in the process. Such matrix material is useful as a binder and imparts greater resistance to the catalyst for the severe temperature, pressure and reactant feed stream velocity conditions encountered in many conversion processes.

Useful matrix materials included both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, kickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alimina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely, with the zeolite content ranging from between about 1 to about 99 percent by weight and more usually in the range of about 25 to about 65 percent by weight of the dry composite.

The $C_3+$ feed stream to the process of this invention contains at least 50% by weight of at least one aliphatic hydrocarbon containing 3 to 12 carbon atoms. The hydrocarbon may be straight chain, open or cyclic and may be saturated or unsaturated. Some contemplated hydrocarbons are propane, propylene, n-butane, n-butenes, isobutane, isobutene, and straight- and branch-chain and cyclic pentanes, pentenes, hexanes, hexenes, heptanes, heptenes, octanes, octenes, nonanes, nonenes, decanes and decenes. The process is particularly useful for the conversion of a feedstock containing at least about 75 wt. % of $C_5$–$C_8$ paraffins.

By the term "$C_3+$ feedstock" is meant a feedstock containing no more than a trace, e.g. about 0.5 wt. % of $C_1$ or $C_2$ hydrocarbons. Preferably, the feedstock consists of hydrocarbons containing at least three carbon atoms.

The process of this invention is conducted so that the feed is contacted with a catalyst of this invention in a reaction zone, such as, for example, a fixed bed of catalyst composition under conversion conditions of such severity as to bring about a conversion of at least about 80 wt. %, preferably at least about 85 wt. % of said aliphatic hydrocarbons. The "severity" of the conditions refers to the cumulative effect of such conditions in causing the reaction to proceed to higher conversions. Thus, the severity is increased by an increase in temperature or pressure, and/or a decrease in space velocity. In a typical embodiment of the process in this invention, the feed stream is introduced into the reaction zone at a temperature within the range of about 450° C. to 700° C., preferably about 500° to 650° C. and more preferably about 525° to 600° C., a pressure within the range of about one-half atmosphere to 1000 psig, preferably about one atmosphere to 500 psig, and more preferably about one atmosphere to 100 psig, and a WHSV of about 0.1 to 50, preferably about 0.1 to 20, and more preferably about 0.5 to 5.

The effluent from the reaction zone is separated and distilled to remove the desired aromatic product and the remainder is recycled for further reaction.

The process of this invention may be carried out with the catalyst in the form of a fixed, moving, or fluidized bed.

The following examples further illustrate the invention. Examples 1 and 2 are embodiments of processes carried out within the invention, while Comparative Examples A to C are similar embodiments which show the results obtained when at least one condition of the invention is not satisfied.

COMPARATIVE EXAMPLE A

Ten grams of a zeolite composition comprising 25 wt. % of a ZSM-5 zeolite having a silica/alumina molar ratio of 55:1 and prepared as described in European Patent Application No. 130,809, the entire disclosure of which is incorporated by reference, and 75 wt. % of kaolin as a binder, were calcined in air to 500° C. for 5 hours to remove any residual organic matter. This "unloaded zeolite" was then exchanged with 50 ml. of 0.5M aqueous ammonia solution at 90° C. for 4 hours, washed with deionized water, and again exchanged with the same ammonia solution overnight at room temperature. After this, the zeolite was again washed with deionized water, dried under vacuum, and exchanged with 30 ml. of 0.35M aqueous $Ga(NO_3)_3$ solution at reflux for 3 hours. After washing the zeolite three times with 50 ml. of deionized water, it was exchanged again with the 0.35M $Ga(NO_3)_3$ solution as described and again washed with deionized water as described. This gallium-exchanged zeolite was dried under 74 mm. Hg vacuum at 90° C. overnight and calcined in air at 500° C. in a muffle furnace for 5 hours to obtain a gallium-loaded, ZSM-5 zeolite catalyst containing 1.94% of gallium based on the weight of the catalyst.

The foregoing catalyst was tested in a laboratory microreactor by contacting 10 grams of the catalyst at 550° C. and atmospheric pressure with a highly paraffinic feedstock which had been vaporized and heated to reactor temperature. The feedstock had the composition indicated in Table I.

TABLE I

| Component | Wt. % |
|---|---|
| $C_4$ Aliphatics | 0.1 |
| $C_5$ Aliphatics | 4.7 |
| $C_6$ Paraffins | 51.4 |
| $C_6$ Olefins & Naphthenes | 3.4 |
| $C_7$ Paraffins | 32.3 |
| $C_7$ Olefins & Naphthenes | 0.3 |
| $C_8$ Aliphatics | 1.2 |
| $C_{9+}$ Aliphatics | 2.3 |
| Benzene | 0.2 |
| Toluene | 4.0 |
| Xylenes | 0.1 |

The feed stream was passed over the catalyst at a WHSV (including binder) of 0.63 which resulted in an reaction time of 17.7 seconds. After various times on stream, the product was analyzed. Hydrogen and light gases ($C_1$-$C_3$) were analyzed by a refinery gas analysis GC, and complete hydrocarbon analysis was obtained on a CP Sil 5CB capillary column. The results are shown in Table 2, where "PON conversion" is the percent conversion of the total of the paraffins, olefins and naphthenes in the feed to any products, the selectivity of any of the indicated products is the percentage by weight of that product based on the total products resulting from the PON conversion, and "BTX" is the total of the $C_6$-$C_8$ aromatics produced, including benzene, toluene, xylenes, and ethyl benzene. The other listed product components are self-explanatory.

TABLE II

| Time on Stream, hrs | 0.9 | 2.3 | 3.8 |
|---|---|---|---|
| PON Conversion, % | 95.2 | 93.0 | 89.7 |
| Selectivity, wt. % | | | |
| BTX | 48.2 | 49.1 | 47.1 |
| $C_2$-$C_4$ Olefins | 5.2 | 6.3 | 8.9 |
| $C_{9+}$ Aromatics | 12.3 | 11.5 | 10.5 |
| $C_1$ + $C_2$ Paraffins | 16.9 | 15.7 | 15.4 |
| Propane | 14.0 | 14.2 | 15.1 |

EXAMPLE 1

The procedure of Comparative Example A was followed except that the described gallium-loaded ZSM-5 zeolite catalyst was calcined in flowing air at 800° C. for one hour before use. The content was unchanged. The results are shown in Table III.

TABLE III

| Time on Stream, hrs. | 1.6 | 3.1 | 4.6 | 6.1 | 7.7 |
|---|---|---|---|---|---|
| PON Conversion, % | 90.9 | 88.2 | 86.7 | 85.4 | 84.3 |
| Selectivity, wt. % | | | | | |
| BTX | 55.2 | 53.3 | 52.5 | 51.6 | 50.9 |
| $C_2$-$C_4$ Olefins | 7.2 | 9.7 | 11.1 | 12.6 | 13.6 |
| $C_{9+}$ Aromatics | 8.6 | 8.3 | 8.4 | 8.4 | 8.5 |
| $C_1$ + $C_2$ Paraffins | 12.6 | 12.5 | 12.1 | 11.9 | 11.7 |
| Propane | 13.0 | 12.8 | 12.4 | 12.2 | 12.1 |

EXAMPLE 2

The procedure of Comparative Example A was followed except that the ZSM-5 zeolite was exchanged only once with $Ga(N_3)_3$ solution as described, to prepare a gallium-loaded ZSM-5 zeolite, containing 1.1% of gallium based on the weight of the catalyst, which was calcined in flowing air at 800° C. for one hour, and the feed stream was passed over the catalyst bed at a WHSV of 0.66 for a reaction time of 17.0 seconds. The results are shown in Table IV:

TABLE IV

| Time on Stream, hrs. | 0.4 | 1.9 | 3.4 | 4.9 | 6.4 |
|---|---|---|---|---|---|
| PON Conversion, % | 96.1 | 93.6 | 91.9 | 91.6 | 90.8 |
| Selectivity, wt. % | | | | | |
| BTX | 54.9 | 52.9 | 52.7 | 52.7 | 52.4 |
| $C_2$-$C_4$ Olefins | 5.2 | 7.6 | 9.4 | 9.7 | 10.6 |
| $C_{9+}$ Aromatics | 7.9 | 8.7 | 6.3 | 6.5 | 6.8 |
| $C_1$ + $C_2$ Paraffins | 15.3 | 14.5 | 14.7 | 14.5 | 14.0 |
| Propane | 13.2 | 12.9 | 13.4 | 13.2 | 12.9 |

Comparison of the results of Comparative Example A, wherein the gallium-loaded ZSM-5 was not calcined at 800° C., with those of Examples 1 and 2 wherein the gallium-loaded zeolite was calcined at 800° C., indicates that calcining the gallium-loaded zeolite at a temperature of at least 700° C., e.g., 800° C., results in higher selectivities to BTX aromatics than are obtained when calcination of the gallium-loaded zeolite at a temperature of at least 700° C. is not carried out.

Selectivities similar to those of Examples 1 and 2 were obtained when the gallium was loaded on the ZSM-5 zeolite by impregnation rather than ion exchange.

COMPARATIVE EXAMPLE B

The procedure of Comparative Example A was followed except that the ZSM-5 zeolite after being calcined at 500° C. to remove residual organics and before being exchanged with gallium, was calcined in flowing air at 850° C. for one hour. The gallium-loaded catalyst contained 0.92% gallium based on the weight of the catalyst. As in Comparative Example A, there was no calcining of the catalyst at 800° C. after the exchange with gallium. In addition, in order to obtain equivalent conversions, the feedstock was passed over the catalyst at a much lower WHSV of 0.14, resulting in a reaction time of 78.8 seconds. The results are shown in Table V:

TABLE V

| Time on Stream, hrs. | 1.2 | 2.7 | 4.2 | 5.7 | 7.2 | 9.1 |
|---|---|---|---|---|---|---|
| PON Conversion, % | 96.2 | 94.3 | 93.3 | 91.9 | 91.9 | 89.5 |
| Selectivity, wt. % | | | | | | |
| BTX | 55.7 | 51.4 | 51.8 | 49.8 | 51.6 | 45.7 |
| $C_2$-$C_4$ Olefins | 1.3 | 2.1 | 2.4 | 3.1 | 3.2 | 4.5 |
| $C_{9+}$ Aromatics | 8.1 | 10.8 | 11.0 | 13.2 | 9.8 | 9.4 |
| $C_1$ + $C_2$ Paraffins | 15.6 | 15.7 | 14.8 | 14.2 | 15.0 | 16.8 |
| Propane | 14.4 | 14.1 | 13.4 | 12.6 | 13.0 | 14.4 |

COMPARATIVE EXAMPLE C

The procedure of Comparative Example B was followed except that the feed rate was 0.31 WHSV equivalent to a reaction time of 36.7 seconds. The results are shown Table VI:

TABLE VI

| Time on Stream, hrs. | 2.4 | 3.9 | 5.4 | 6.9 | 8.6 |
|---|---|---|---|---|---|
| PON Conversion, % | 85.9 | 84.1 | 81.4 | 80.0 | 78.6 |
| Selectivity, wt. % | | | | | |
| BTX | 52.6 | 52.1 | 51.1 | 50.6 | 49.9 |
| $C_2$-$C_4$ Olefins | 9.0 | 10.5 | 12.1 | 13.3 | 14.2 |
| $C_{9+}$ Aromatics | 8.1 | 8.4 | 8.3 | 8.3 | 8.0 |
| $C_1$ + $C_2$ Paraffins | 14.2 | 13.7 | 13.5 | 13.3 | 13.3 |

TABLE VI-continued

| | | | | | |
|---|---|---|---|---|---|
| Propane | 13.1 | 12.3 | 11.9 | 11.7 | 11.7 |

A comparison of the results of Examples 1 and 2 with those of Comparative Examples B and C shows that the catalyst of this invention has substantially greater activity for the aromatization of feedstocks having a high proportion of $C_2$–$C_{12}$ aliphatics, with equivalent or better BTX selectivity, than a gallium-loaded catalyst prepared by calcining a similar ZSM-5 zeolite at a temperature higher than 700° C. before rather than after loading the zeolite with gallium. That the latter catalyst has substantially lower activity than the catalyst of the invention is confirmed by comparing the results of Comparative Examples B and C, where, when the feed rate was raised from 0.14 WHSV in Comparative Example B to 0.31 WHSV in Comparative Example C (which was still less than one half that of Examples 1 and 2), the PON conversion activity of the catalyst dropped considerably without any significant increase in BTX selectivity.

I claim:

1. A process for producing aromatic compounds which comprises contacting a $C_3^+$ feed containing at least 50 weight percent of $C_3$ to $C_{12}$ aliphatic hydrocarbons under conversion conditions of a severity resulting in a conversion of least about 80 wt. % of said hydrocarbons, with a catalyst prepared by loading with gallium a zeolite characterized by a Constraint Index within the approximate range of 1 to 12 and having a silica/alumina ratio of about 25:1 to 1000:1, and subsequently calcining the catalyst at a temperature of at least about 700° C.

2. The process of claim 1 wherein said zeolite has the structure of ZSM-5.

3. The process of claim 1 wherein the gallium is loaded onto the zeolite by ion-exchange or impregnation.

4. The process of claim 3 wherein the gallium is loaded in an amount of about 0.5 to 5% based on the weight of the catalyst.

5. The process of claim 3 wherein said calcining is carried out at a temperature of at least about 775° C.

6. The process of claim 5 wherein said calcining is carried out at a temperature of at least about 800° C.

7. The process of claim 3 wherein said calcining is carried out at a temperature of about 800° to 825° C. for a period of about 1 to 1.5 hours.

8. The process of claim 1 wherein the conversion conditions include a temperature of from about 450° C. to about 700° C., a pressure of from about one atmosphere to about 1000 psig, and a WHSV of from about 0.1 to about 50.

9. The process of claim 8 wherein the temperature is about 500° to 650° C., the pressure is about one atmosphere to 500 psig, and the WHSV is about 0.1 to 20.

10. The process of claim 9 wherein the temperature is about 525° to 600° C., the pressure is about one atmosphere to 100 psig, and the WHSV is about 0.5 to 5.

11. The process of claim 8 wherein the catalyst is employed in the form of a fixed bed.

12. The process of claim 8 wherein the catalyst is employed in the form of a fluid bed.

13. The process of claim 8 wherein the catalyst is employed in the form of a moving bed.

14. The process of claim 1 wherein said aliphatic hydrocarbons comprise at least about 75 wt. % of $C_5$–$C_8$ paraffins.

* * * * *

UNITED STATES PATENT AND TRADEMARK OFFICE
CERTIFICATE OF CORRECTION

PATENT NO. : 4,861,933
DATED : August 29, 1989
INVENTOR(S) : M. Nemet-Mavrodin

It is certified that error appears in the above-identified patent and that said Letters Patent is hereby corrected as shown below:

Col. 5, Table, line 4   "(477°C)" should be --(427°C)--

Signed and Sealed this

Twenty-fifth Day of September, 1990

Attest:

HARRY F. MANBECK, JR.

*Attesting Officer*          *Commissioner of Patents and Trademarks*